(12) United States Patent
Nace

(10) Patent No.: US 8,945,035 B2
(45) Date of Patent: Feb. 3, 2015

(54) KNEE BRACE WITH IMPROVED GAIT SWING ASSIST

(71) Applicant: Richard A. Nace, San Jose (CR)

(72) Inventor: Richard A. Nace, San Jose (CR)

(*) Notice: Subject to any disclaimer, the term of this patent is extended or adjusted under 35 U.S.C. 154(b) by 20 days.

(21) Appl. No.: 13/648,498

(22) Filed: Oct. 10, 2012

(65) Prior Publication Data

US 2013/0035623 A1  Feb. 7, 2013

Related U.S. Application Data

(63) Continuation-in-part of application No. 13/178,447, filed on Jul. 7, 2011, now Pat. No. 8,376,974, and a continuation-in-part of application No. 12/469,671, filed on May 20, 2009, now Pat. No. 8,308,669, and a continuation-in-part of application No. 12/200,394, filed on Aug. 28, 2008, now Pat. No. 8,308,671.

(51) Int. Cl.
*A61F 5/00* (2006.01)

(52) U.S. Cl.
USPC .............................................. 602/23; 602/26

(58) Field of Classification Search
CPC ....... A61F 5/0106; A61F 2/64; A61F 5/0104; A61F 2002/5004; A61F 2002/5033; A61F 2002/5073; A61F 2002/6818; A61F 2002/704; A61F 2002/705; A61F 2002/7625; A61F 2002/7635; A61F 2002/7645

USPC ............ 128/882; 602/5, 16, 23, 26–28; 5/624
See application file for complete search history.

(56) References Cited

U.S. PATENT DOCUMENTS

| 4,503,846 | A | 3/1985 | Martin |
| 4,606,542 | A | 8/1986 | Segal |
| 4,991,571 | A | 2/1991 | Kausek |
| 5,415,625 | A | 5/1995 | Cassford et al. |
| 5,542,911 | A * | 8/1996 | Cassford et al. ................ 602/26 |
| RE37,209 | E | 6/2001 | Hensley et al. |
| 6,527,733 | B1 * | 3/2003 | Ceriani et al. ................... 602/16 |
| 8,216,165 | B2 * | 7/2012 | Ravikumar et al. ............. 602/13 |
| 8,235,869 | B2 * | 8/2012 | Rastegar et al. ................. 482/2 |
| 2002/0133108 | A1 | 9/2002 | Jagodzinski |
| 2004/0064195 | A1 * | 4/2004 | Herr ................................. 623/24 |
| 2004/0243253 | A1 * | 12/2004 | Cool et al. ....................... 623/52 |
| 2006/0142680 | A1 * | 6/2006 | Iarocci ............................ 602/16 |

* cited by examiner

*Primary Examiner* — Michael A. Brown
(74) *Attorney, Agent, or Firm* — Larson & Larson, P.A.; Justin P. Miller; Patrick A. Reid

(57) ABSTRACT

A knee brace including a swing assist system for the storage and return of energy is disclosed. The knee brace optionally includes bladders for the application of pressure to the knee joint and/or shin of a patient. An optional swing assist mechanism is present at the hinge(s) of the brace, aiding in the extension of the patient's leg and, therefore, correcting the patient's gait.

12 Claims, 4 Drawing Sheets

KNEE BRACE WITH IMPROVED GAIT SWING ASSIST

CROSS-REFERENCE TO RELATED APPLICATION

This application is continuation-in-part of U.S. patent application Ser. No. 12/200,394, filed Aug. 28, 2008, a continuation-in-part of U.S. patent application Ser. No. 12/469,671, filed May 20, 2009, and a continuation-in-part of U.S. patent application Ser. No. 13/178,447, filed Jul. 7, 2011, the disclosures of which are hereby incorporated by reference.

FIELD

The invention relates to knee braces.

BACKGROUND

Orthotic devices and appliances, commonly referred to as "orthotics," have been utilized for many years by orthotists, physical therapists, and occupational therapists. Orthotics assist in the rehabilitation of a patient's joints and associated skeletal systems. Generally orthotics act to support and protect the joint, while alleviating pain associated with joint movement.

There are multiple types of osteoarthritis with different effects on the human knee joint.

Primary osteoarthritis is usually related to aging. With aging the water content of the cartilage increases and the protein makeup of the cartilage degenerates. Repetitive use of the joints over the years can irritate and inflame the cartilage, causing joint pain and swelling. Eventually, cartilage begins to degenerate by flaking or forming tiny crevasses. In advanced cases, there is a total loss of cartilage cushion between the femur and tibia bones at the knee joint. This loss leads to diminished joint space on the affected side of the knee, in turn causing pain and joint mobility limitations. Inflammation of the cartilage can also stimulate new bone outgrowths, or spurs, to form around the joints, in turn causing increased pain and joint inflammation.

Important components of patient care include minimizing the progression of the damage to the cartilage of the knee joint and preventing the formation of bone spurs from bone-on-bone contact during knee joint bending. In a normal knee the soft cartilage layers between the femur (upper leg bone of the knee) and the tibia (lower leg bone of the knee) are separated by a thin layer of synovial fluid. The synovial fluid provides lubrication and prevents direct contact between the cartilage layers.

In a patient with osteoarthritis or osteoarthrosis the cartilage has degraded. The result is no longer smooth cartilage surfaces sliding across one-another while lubricated by synovial fluid, but instead rough cartilage surfaces rubbing against one another directly. This rubbing is the source of osteoarthritis/osteoarthrosis pain.

Bone spurs may form as a result of this joint irritation. These bone spurs sometimes cause bits of bone and cartilage to detach. These detached pieces of bone float within the knee joint, causing further damage.

Damage to the knee is often isolated to a certain portion of the knee joint. In fact, the most common form of osteoarthritis or osteoarthrosis is unicompartmental, meaning that only one of the three compartments of the knee joint is significantly affected by the loss of cartilage padding.

The human knee has three compartments. The medial compartment of is on the inside of the centerline of the body, closest to the knee of the other leg. The lateral compartment of the knee is furthest from the centerline of the body. Finally, the patellar compartment is in the center-upper portion of the knee, to the rear of the patella or knee cap.

The majority of osteoarthritis cases are medial compartment degeneration. Thus, the cartilage or cushioning of the knee joint has significantly deteriorated on the inside portion of the knee. As a result of cartilage degeneration within the medial compartment of the knee the knee becomes imbalanced. The imbalance results in a knee that bows outward. This is often called a "bowleg" condition, referred to as a varus deformity of the knee joint, or genu varum.

A knee joint with bowleg deformity places significant force on the medial compartment of the knee, resulting in joint pain.

Alternatively, a patient will have damage to the lateral compartment of the knee. The result is again an unbalanced knee, with the knee bending inwards at the knee joint. The result is a knock-kneed appearance, or valgus deformity of the knee joint.

SUMMARY

Osteoarthritis knee braces are designed to do two things: First, correct the abnormal bending of the knee joint inwards or outwards (valgus or varus correction). Secondly, many osteoarthritis knee orthotics or braces are designed to prevent the bone-on-bone contact of the femur and tibia bones in the medial or lateral compartment of the knee joint as the patient bears weight during walking. This action of lifting femur, pulling down the tibia, or keeping the femur and tibia bones from coming in contact during the straightening of the knee during heel strike is often called "unloading" the knee joint. By unloading the knee joint, the constant irritation of the degenerated cartilage in the affected compartment of the knee (medial or lateral) can reduced, leading to a significant reduction in pain.

Prior art braces accomplish this unloading through the use of long struts acting as lever arms, with fulcrums located at the knee joint. Through the use of mechanical means the fulcrum is forced against the knee joint, providing inward force.

In contrast, the disclosed knee brace does not required the use of long struts and mechanical means to provide a lifting force to the knee. Instead, air bladders present at the knee joint provide inward force. No long lever arm is required, resulting in a shorter and more compact knee brace. This reduces weight, as well as the area of the user's leg that is subjected to pressure from the brace. The shorter and more compact brace migrates less on the leg, and as a result does not slip out of position.

The use of air bladders also allows for the day-to-day adjustment required by patients. Prior art systems with complicated mechanical means for setting require that adjustment be performed only by an orthotist. But the human body is not static. Muscle mass increases over the period of time the brace is in use, swelling fluctuates, water retention varies. The disclosed knee brace allows the user to adjust the pressure created by the air bladders to match the needs of the day.

When addressing knee problems, the old methodology was to operate on a patient, fit the patient with a brace, and use the brace to force the patient to correct her gait. This is a process fraught with problems. Knee problems do not appear quickly, but develop over years of gradual degradation. During this time the patient slowly and subtly alters her gait to compensate for the discomfort caused by the damage.

As a result, by the time the knee pain rises to a level that requires surgery the patient has been walking incorrectly for years. Thus, when the patient begins to walk after surgery her gait is still improper despite the surgical correction of the problem.

The answer is use of the disclosed knee brace prior to surgery. The disclosed knee brace effectively reduces the pain and discomfort within the joint. When used in conjunction with the swing assist system discussed below, the patient begins to correct her gait before surgery. The result is healthier leg muscle and connective tissue, stronger bones, and a proper gait. The healthier tissue provides the surgeon with better structure for replacement of the knee. And the corrected gait allows the patient to recover more quickly, starting to walk on her new knee with the correct gait.

An important component of correcting a patient's gait is enabling full extension of the patient's leg, where the knee joint is as open as possible without hyperextension. Many patients have significant trouble extending their legs fully as a result of weak muscles, past pain, and joint inflexibility. When a patient achieves full extension of her leg while walking, the result is a proper heel-to-toe gait. A heel-to-toe gait starts when the heel of the foot contacts the ground first, followed by transitioning weight to the midfoot, with the toes being the final point of contact between the foot and the ground. Incorrect gait is often the result of joint injury/damage.

A patient with medial compartment osteoarthritis will land on the lateral (outside) portion of the heel/foot during her stride. This is a result of an attempt to shift the load from the affected side of the knee, the medial side, to the unaffected side of the knee, the lateral side.

The consequences of this imperfect gait are twofold: First, the patient's muscle memory that controls the precise firing sequence for walking becomes altered. Second, the medial quadriceps muscles and Vastus Medialis Obliquus (VMO) muscles are less excited by this altered gait, and thus less exercised. It is this second factor that results in the loss of muscle mass, decreases support of the knee joint, and exacerbates damage to the knee joint.

The combination of eliminating pain associated with gait, while aiding in the extension of the lower leg, can correct the damaged gait mechanics of a patient.

With the disclosed knee brace correcting the patient's gait, and the repetitive nature of walking, over time the patient's muscle memory is corrected. This muscle memory correction causes the nerves to activate the proper muscles for a healthy gait. Activation of the proper muscles results in strengthening, and an eventual return to normal muscle structure.

The patient then experiences the proper heel to toe gait where she lands her the center of her heel at the termination of the swing phase of her gait, transition the weight down the centerline of her foot, and ends the gait by coming off of her toes.

For some patients, the rehabilitative effect of the disclosed knee brace can allow for removal of the brace and the corrected gait will be maintained.

The disclosed knee brace uses a swing assist system to help the patient achieve full extension, and thus the proper heel-to-toe gait. The swing assist system includes an energy storage member that extends across the hinge, connecting the upper portion of the support arm to the lower portion of the support arm. The energy storage member gathers energy during flexion of the knee joint and releases it during extension. The result is an improvement in leg extension, even for patients who lack the strength or conditioning to achieve full leg extension in the absence of the disclosed knee brace.

The swing assist system is installed on one or both of the hinges. There is no requirement that both hinges have a swing assist system, although such an arrangement is likely to produce the most balanced force during extension and flexion of the knee brace.

The energy storage member of the swing assist system is any device capable of repeatedly storing and releasing rotational energy. Such devices include elastic/rubber bands, elastic/rubber loops, o-rings, o-ring cord stock, torsion springs, coil springs, and all other similar devices.

The energy storage member attaches to the strut above and below the hinge, or to an extension of the strut above and below the hinge. The energy storage member location relative to the hinge is dependent on the location from which it can best provide energy storage and return. If the energy storage member is an elastic band, it is likely best located on the anterior side of the hinge. If it is a coil spring that is to be extended during flexion, then it is best located on the anterior side of the hinge. If it is a coil spring to be compressed during flexion, it is best located on the posterior side of the hinge.

Energy storage members that store energy through rotation are likely best located at the rotational center of the hinge.

The exemplary embodiment included in the below referenced figures uses a looped elastic band as the energy storage member.

The exemplary knee brace shown in the figures supports and captures the energy storage member in a channel. Rather than using individual setting blocks on the exterior surface of the hinge, the disclosed knee brace uses a channel that is integral to the hinge. Integrating the swing assist mechanism and the hinge was disclosed in the parent patent applications referenced above.

The integral channel for support of the energy storage member does not allow for the removal/replacement of setting blocks in order to increase/decrease the tension of the elastic member and, therefore, the resulting force. But patient trials showed that patients did not favor a reduction in swing assist force. Instead, it was found that altering the force provided by the swing assist system was counter-productive, requiring the patient to relearn the correct gait. Thus, an integrated swing assist system was created.

Alternative arrangements exist where support for the energy storage member is not required. The example energy storage member is a looped elastic band, supported across the hinges by the integral channel. Removal of the support allows the looped elastic band to act between the two attachment points.

The appropriate location for each of the one more air bladders varies depending upon the injury to be treated.

For the sake of simplicity, the interior of the knee joint will be discussed in terms of medial and lateral compartments. The medial compartment is the interior portion of the knee. For the right knee of a patient, this is the left portion of the knee joint. The lateral compartment is the exterior portion of the knee. For the right knee of a patient, this is the right portion of the knee joint.

If the damage within the knee is general cartilage deterioration, a bladder is needed at both the medial and lateral locations of the leg. Providing simultaneous external forces against both sides of the knee joint unloads the knee joint, creating space between the cartilage surfaces.

Compression of both sides of the knee "distracts" the knee joint. The pressure lifts the femur, creating space in the joint. The pressure acts to stretch the top of the tibia away from the base of the femur. A shock-absorption effect is created by the presence of new space. With the new space in the knee joint, cartilage begins to grow. This new cartilage in turn decreases joint pain and improves function. The space also takes up any laxity in the ligaments, increasing knee stability.

If the knee is carrying its load on the medial side, the knee joint has rolled toward the medial surfaces. This creates space within the lateral side of the knee. Applying force using an air bladder to the lateral side rolls the knee joint toward the lateral side of the knee, creating space in the knee joint.

Correspondingly, if the knee is carrying its load on the lateral side, the knee joint has rolled toward the lateral surfaces. This creates space within the medial side of the knee. Applying force using an air bladder to the medial side rolls the knee joint toward to medial side of the knee, creating space in the knee joint.

Air bladders are optionally located nearer to the shin. If such bladders are included, they are always located on the lateral side of the brace. From the lateral position the bladder can help the leg to swing properly, acting to bring the lower portion of the leg toward the midline of the body.

The determination of which straps are necessary for support of the knee requires knowledge of what damage the knee suffered. If the damage is only to the cartilage of the knee, the forces to be controlled are lateral forces and no straps are needed beyond those opposing the upper and lower cuffs. If instead the damage is to the ACL (Anterior Cruciate Ligament) the upper and lower portions of the knee joint can move relative to one another in the anterior/posterior directions. The brace must then prevent forward translation of the tibia (lower leg bone) relative to the femur (upper leg bone). An ACL tear removes the ligament that prevents the lower leg bone from moving too far forward. The result of such movement is significant pain and further knee injury. The addition of a strap below the knee provides support that the ACL can no longer create.

The fit of any brace to the patient is important for both patient comfort and brace effectiveness. A brace that is too tight is uncomfortable because it cuts into the patient's tissue. A brace that is too loose is ineffective because it cannot support the load of the knee, and does not maintain the alignment necessary to encourage proper bending location.

But a proper fit is difficult. Muscle atrophy of one leg may result in legs of differing diameters. During the process of prehabilitation/rehabilitation the creation of new muscle mass will cause an increase in leg diameter, further complicating orthotic sizing. If the changes to muscle size exceed the amount that can be adjusted using the straps the patient must purchase an additional orthotic. This is expensive and wasteful.

The addition of holes to the upper cuff increases the span of sizes over which a single brace can be used. This decreases the number of braces that an orthotist must keep on hand, and allows for nuanced sizing to fit each specific patient. As a result, a patient can be fitted with an off-the-shelf brace that as well as a custom brace.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
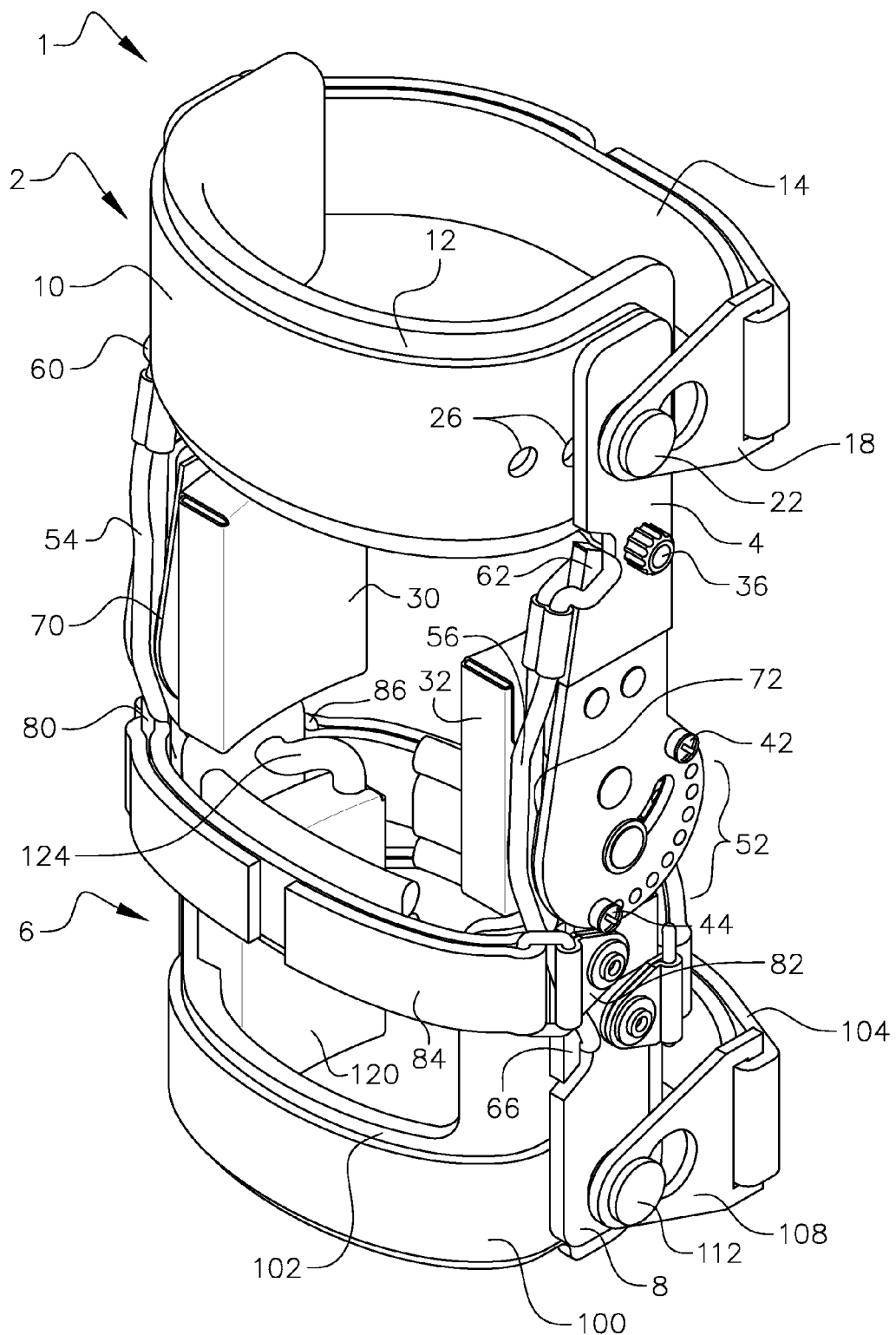
FIG. 1 illustrates a first view of the knee brace.

Reference will now be made in detail to the presently preferred embodiments of the invention, examples of which are illustrated in the accompanying drawings. Throughout the following detailed description, the same reference numerals refer to the same elements in all figures.

Figure 2:
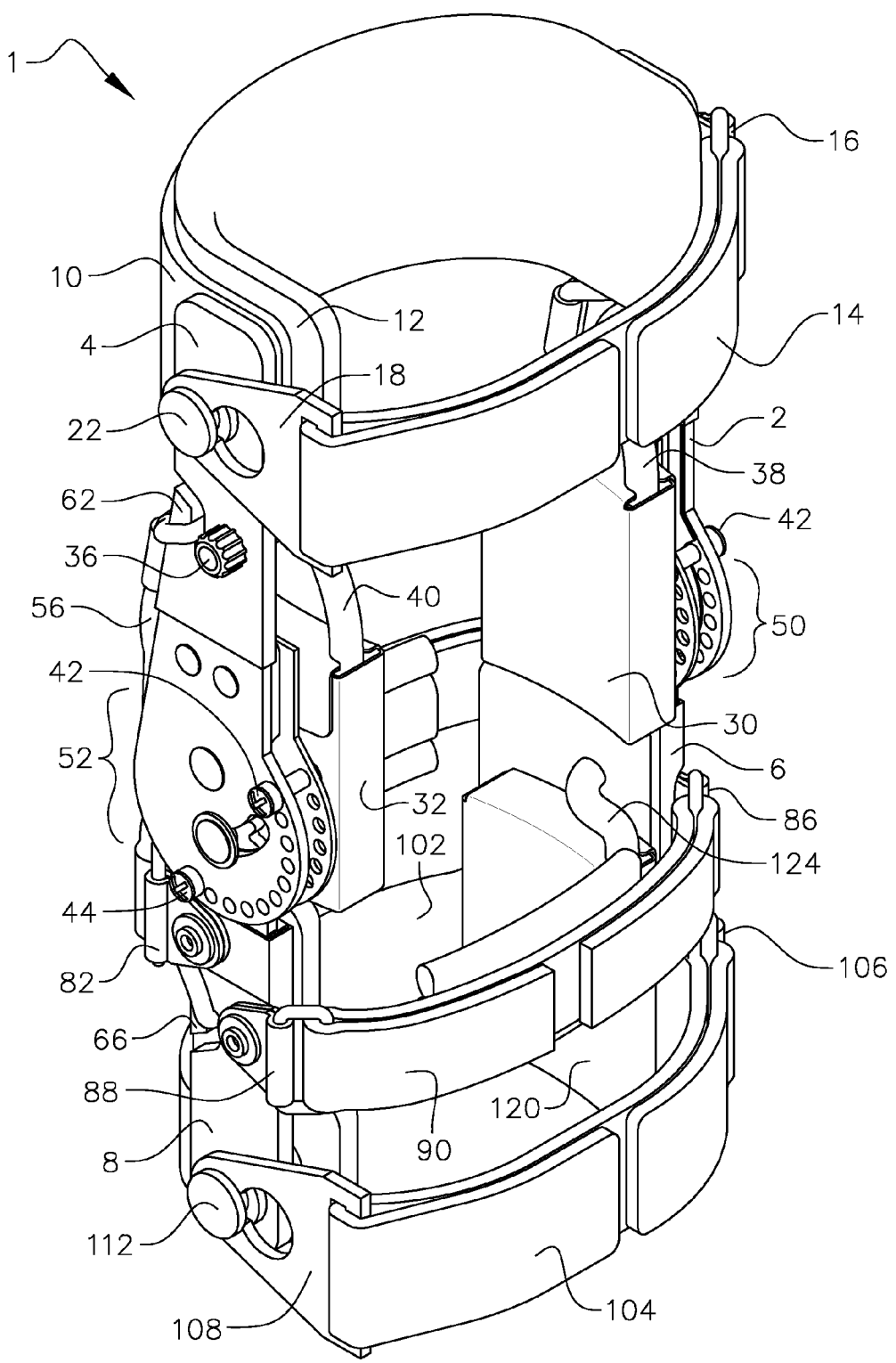
FIG. 2 illustrates a second view of the knee brace.

Referring to FIGS. 1 and 2, the knee brace 1 will be disclosed. The knee brace 1 is intended to be worn across the knee joint of a patient's leg. The support structure of the knee brace 1 is comprised of a first upper support arm 2, second upper support arm 4, first lower support arm 6, and a second lower support arm 8. The support arms 2/4/6/8 are substantially parallel to the leg bones and provide rigid support for the remaining portions of the knee brace 1.

The first upper support arm 2 and second upper support arm 4 are connected across a patient's thigh on the anterior side of the knee brace 1 by a flexible upper cuff 10. An upper cuff pad 12 provides cushion between the patient's leg and the flexible upper cuff 10. On the posterior side of the knee brace 1 is an upper cuff strap 14, engaging with the first upper support arm 2 through a first upper clip 16, in turn engaging a first upper pin 20 (not shown). On the other side of the brace, the upper cuff strap 14 engages with the second upper support arm 4 through a second upper clip 18, in turn engaging a second upper pin 22.

As discussed above, allowing for adjustment of the flexible upper cuff 10 sizing results in a knee brace 1 that is tailored to the leg size and shape of the specific patient, as well as that specific patient's stage of prehabilitation/rehabilitation. This adjustable sizing is accomplished by the inclusion of a first set of upper cuff adjustment holes 24 (not shown) and a second set of upper cuff adjustment holes 26. The upper pins 20/22 are removable, allowing for the position of the flexible upper cuff 10 to be adjusted and then held in place by the upper pins 20/22. The flexible upper cuff 10 is permitted to rotate about the upper pins 20/22, as is the upper cuff strap 14. This prevents the upper and lower edges of the flexible upper cuff 10 from pressing into the patient's tissue, which in turn causes discomfort.

The first upper support arm 2 meets the first lower support arm 6 at first hinge 50. The second upper support arm 4 meets the second lower support arm 8 at second hinge 52. In the example illustrated the hinges 50/52 are polycentric, having many centers or a center that varies depending on the bend angle. Alternatively, the hinges 50/52 are unicentric, having only a single center. The motion of a polycentric hinge generally better matches that of a human knee.

Adjacent to the first hinge 50, on the inner portion facing the patient's leg, is first knee bladder 30. Adjacent to the second hinge 52, also on the inner portion facing the patient's leg, is second knee bladder 32. As discussed above the number of bladders required is dependent upon the course of treatment. Thus, each bladder 30/32 is optional. To prevent discomfort, if either bladder 30/32 is removed it is optionally replaced with a pad to prevent contact between the patient's knee and the hinge 50/52.

The first knee bladder 30 is filled using the first knee bladder hose 38 connected to the first knee bladder nozzle 34 (not shown). The second knee bladder 32 is filled using the second knee bladder hose 40 connected to the second knee bladder nozzle 36.

Air bladders are optionally located nearer to the shin. The shin bladder 120 is filled using shin bladder hose 124 connected to shin bladder nozzle 122 (not shown). As with the knee bladders 30/32, the amount of air in the shin bladder 120 is adjustable to accommodate differences in swelling and muscle size.

The motion of the knee brace hinges 50/52 is controlled and limited by a number of individual components. Each hinge 50/52 has a flexion limit stop 42 and extension limit stop 44. The flexion limit stops 42 limit the motion of the knee brace 1 at a certain angle to prevent the brace from flexing to a smaller angle. E.g., allowing flexion to a minimum angle of 120 degrees.

Each flexion limit stop 42 is adjustable, allowing the orthotist to adjust and set the flexion limit stop 42 to the point appropriate for the patient's stage of recovery.

The extension limit stops 44 limit the motion of the knee brace 1 at a certain angle to prevent the brace from extending to a larger angle. E.g, allowing extension to a maximum angle of 160 degrees.

As discussed above, the swing assist system corrects a patient's gait by absorbing energy during flexion and releasing it during extension, increasing the patient's leg extension. The result is a proper heel-toe stride.

In the example shown in the figures, the first energy storage member 54 and second energy storage member 56 are elastic bands. There is no requirement that the energy storage members 54/56 be elastic bands. As disclosed above, it is anticipated that the energy storage members 54/56 be any device capable of storing and returning energy. Nor is it required that two energy storage members 54/56 be used. While in some instances the patient's gait is best corrected by use of two energy storage members 54/56, a single energy storage member 54/56 likely provides sufficient benefit to justify use.

Energy storage members 54/56 that do not interface directly with the hinges 50/52 require attachment points. The exemplary elastic bands shown in the figures attach to the support arms at defined points. The first energy storage member 54 attaches to the first upper support arm 2 at the first upper attachment point 60, and to the first lower support arm 6 at the first lower attachment point 64 (not shown). The second energy storage member 56 attaches to the second upper support arm 4 at the second upper attachment point 62, and to the second lower support arm at the second lower attachment point 66.

To ensure consistent action by the energy storage members 54/56 it is useful to guide and contain the energy storage members 54/56. In the example shown in the figures first energy storage member 54 lies partially within a first energy storage member groove 70 and the second energy storage member 56 lies partially within a second energy storage member groove 72. The respective energy storage grooves 70/72 retain their respective energy storage members 54/56 during flexion and extension, with emphasis on maintaining placement during flexion.

In the example shown in the figures, the grooves 70/72 are integrated with the hinges 50/52. In other examples the grooves 70/72 are constructed from multiple individual pieces, such as setting blocks (disclosed in full in the parent applications).

Grooves 70/72 act to keep the energy storage members 54/56 to the front of, or anterior to, the hinges 50/52. The distance between the center of the hinges 50/52 and the surface of the grooves 70/72 affects the behavior of the energy storage members 54/56 during bending. Assuming the energy storage members 54/56 are of a type that requires stretching (e.g., an elastic band), having no distance between the center of the hinges 50/52 and the energy storage members 54/56 will render the energy storage members 54/56 useless because the length of the energy storage members 54/56 will not change during leg flexion.

Furthermore, again assuming the energy storage members 54/56 are of a type that requires stretching (e.g., an elastic band), the energy storage members 54/56 must not cross the center of the hinges 50/52. Allowing the energy storage members 54/56 to cross the center of the hinges 50/52 causes two problems: First, effectiveness is decreased because the energy storage member 54/56 cannot provide consistent force because its change in length is not proportional to the flexion of the brace. Second, after the energy storage members 54/56 crosses the center of the hinges 50/52 it may act to aid flexion, rather than extension, working against the patient rather than helping.

The benefits of integrating the grooves 70/72 and hinges 50/52 include a smaller profile hinge and thus knee brace, simplicity in construction, and a reduction in the number of required parts and fasteners.

As discussed above, optional additional straps are present in front of the patient's shin bone. When the knee injuries include damage to the ACL the use of such a strap helps to stabilize the knee and compensate for the loss.

In the disclosed knee brace 1, the first lower anterior strap bracket 80 connects the lower anterior strap 84 to the second lower anterior strap bracket 82. This strap crosses the anterior portion of the shin bone, preventing the tibia from sliding forward with respect to the femur.

Additionally, there is optionally a corresponding strap across the posterior of the lower leg (shin). The lower posterior strap 90 is connected to the first lower support arm 6 by the first lower posterior strap bracket 86 and to the second lower support arm 8 by the second lower posterior strap bracket 88.

The first lower support arm 6 and second lower support arm 8 are connected across a patient's thigh by flexible lower cuff 100. A lower cuff pad 102 provides cushion between the patient's leg and the flexible lower cuff 100. On the posterior side of the brace is an upper cuff strap 104, engaging with the first lower support arm 6 through a first lower clip 106, in turn engaging a first lower pin 110 (not shown). On the other side of the brace, the lower cuff strap 104 engages with the second lower support arm 8 through a second lower clip 108, in turn engaging a second lower pin 112.

In other examples the flexible lower cuff 100 is only semi-flexible, or rigid. If so, it is sometimes integrated with one of both of the first lower support arm 6 and second lower support arm 8.

Figure 3:
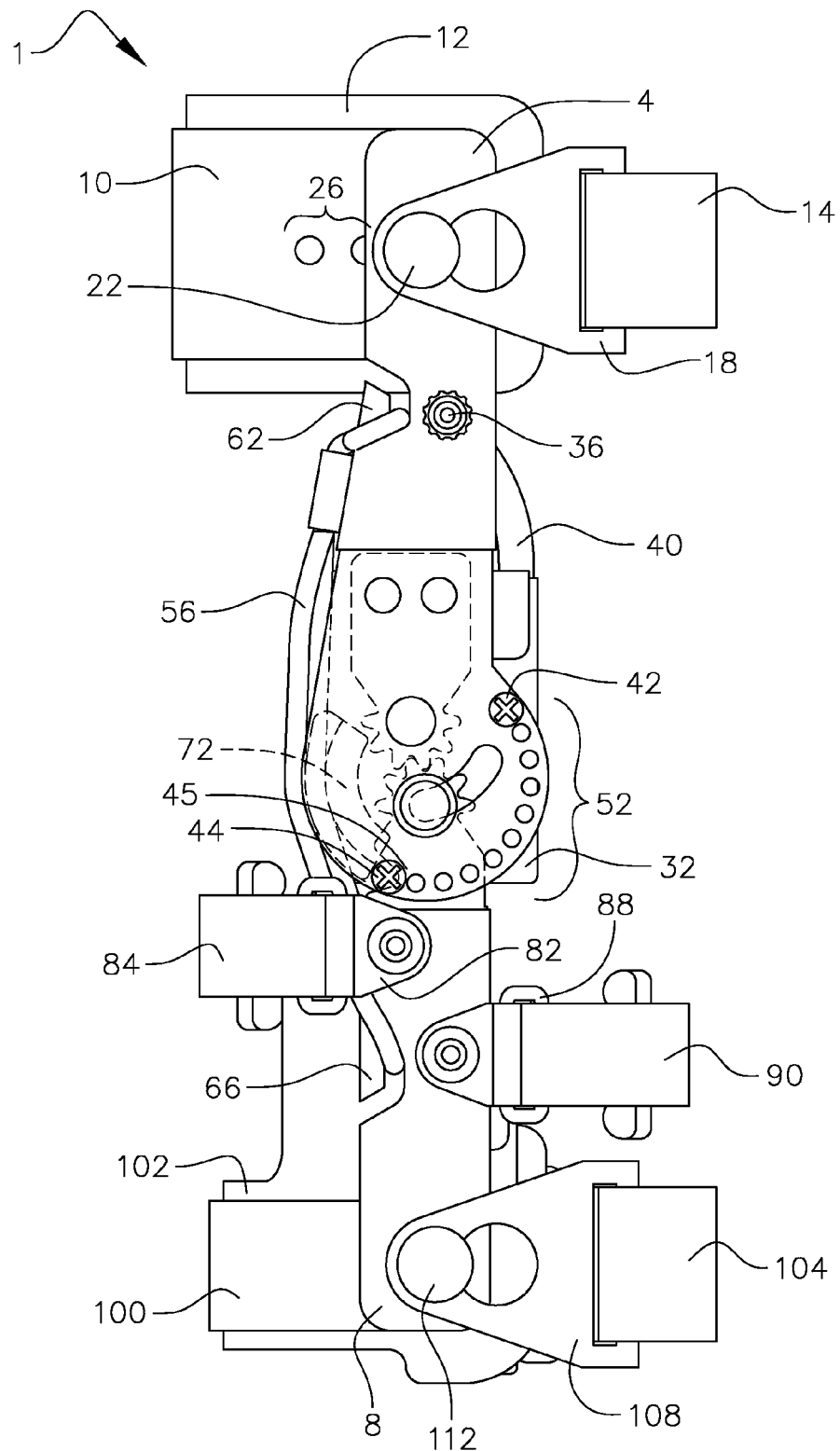
FIG. 3 illustrates the knee brace in a fully extended position.
Figure 4:
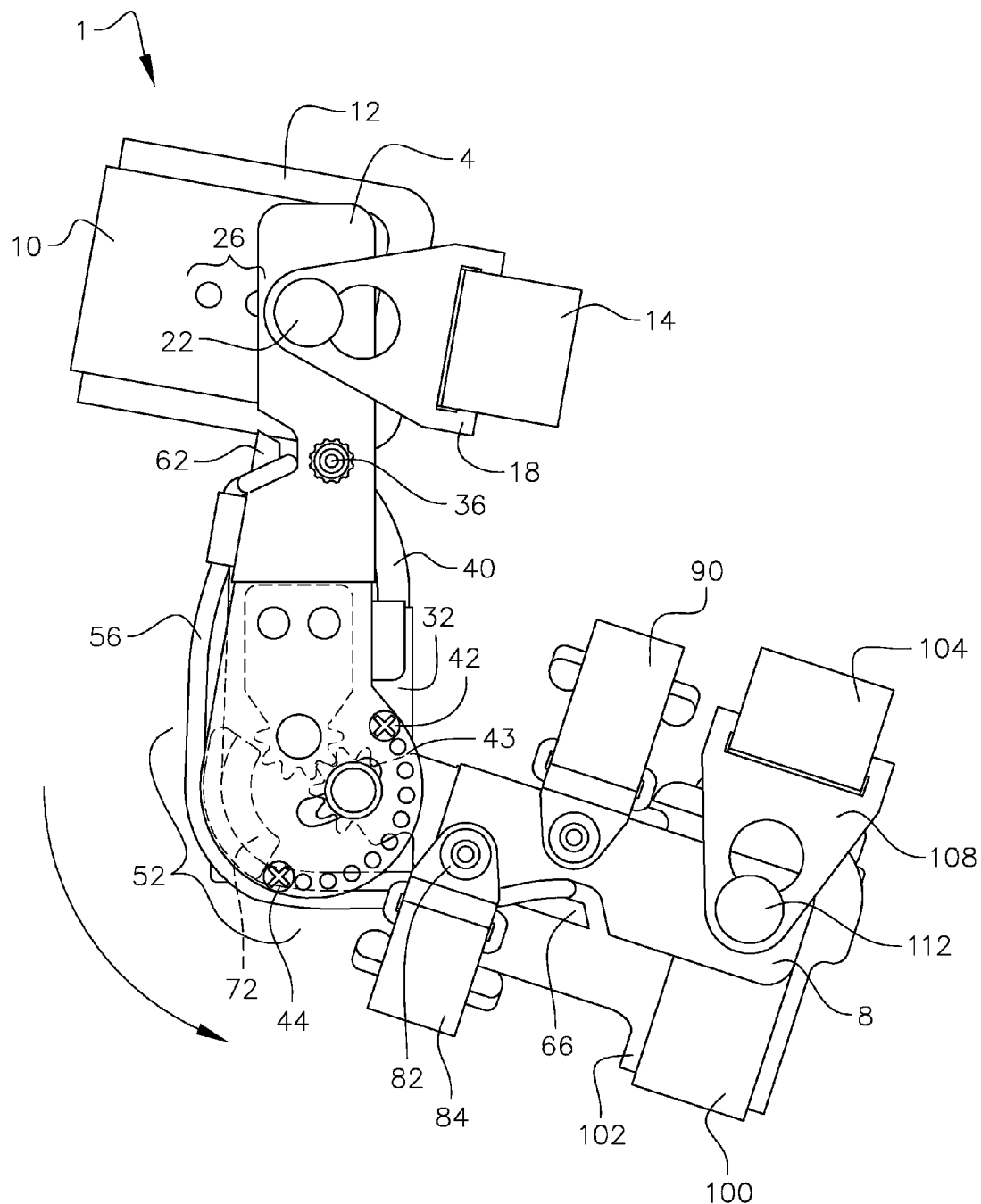
FIG. 4 illustrates the knee brace in a nearly fully flexed position.

Referring to FIGS. 3 and 4, the bending of the knee brace 1 will be described. FIG. 3 shows the knee brace 1 in its fully extended position.

The second lower support arm 8 is contacting the extension stop 44 at extension contact point 45.

FIG. 4 shows the knee brace 1 in its nearly fully flexed position. The second lower support arm 8 is nearly contacting the flexion stop 42 at flexion contact point 43.

A comparison between FIGS. 3 and 4 shows the lengthening of the second energy storage member 56. The energy storage member(s) 54/56 lengthen during flexion, gathering energy that is later released to assist the patient's leg during extension.

In FIG. 3 the flexible upper cuff 10 and upper cuff strap 14 with associated attachment hardware are shown slightly clockwise rotated. This is exemplary only, providing an example of how the rotation of the patient's thigh may be compensated for by the knee brace 1.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A knee brace comprising;
   a. an energy storage mechanism, the energy storage mechanism continuously gathering energy during leg flexion and releasing energy during leg extension;
   b. the energy storage mechanism is an energy storage member and an energy storage member groove, and the energy storage member groove restrains a center portion of the energy storage member during flexion of the knee brace, preventing the energy storage member from crossing a center of a hinge; and
   c. further comprising a pair of air bladders, wherein one of the air bladder is a knee air bladder located at a hinge, and the other air bladder is a shin air bladder located near a distal end of the brace.

2. The knee brace of claim 1, wherein the energy storage mechanism is one or more o-rings.

3. The knee brace of claim 1 wherein an upper cuff includes one or more adjustment holes; and
   the knee brace further comprises a first upper pin and a second upper pin, wherein the first upper pin joins the upper cuff to the upper half through one or more adjustment holes, and the second upper pin joins the upper cuff to the upper half through one or more adjustment holes.

4. A knee brace comprising
   a. an energy storage mechanism, the energy storage mechanism continuously gathering energy during leg flexion and releasing energy during leg extension,
   b. wherein the energy storage mechanism is a first energy storage mechanism and a second energy storage mechanism, the first energy storage mechanism integral to a first hinge, the second energy storage mechanism integral to a second hinge; and
   c. wherein the first energy storage mechanism includes a first elastic band positioned within a first groove associated with the first hinge, and the second energy storage mechanism includes a second elastic band positioned within a second groove associated with the second hinge.

5. A knee brace comprising:
   a first upper support arm, connected to a first lower support arm by a first hinge;
   a second upper support arm, connected to a second lower support arm by a second hinge;
   the first upper support arm connected to the second upper support arm by an upper cuff;
   the first lower support arm connected to the second lower support arm by a lower cuff;
   an energy storage member, the energy storage member attached to only the first upper support arm and the first lower support arm, the energy storage member encouraging the first upper support arm and the first lower support arm into a parallel arrangement; and
   wherein the energy storage member is a selected from one of (i) a looped elastic band, (ii) an o-ring, and (iii) an elastic band with an energy storage member groove.

6. The knee brace of claim 5, wherein the energy storage member is a looped elastic band.

7. The knee brace of claim 6:
   wherein the upper cuff includes one or more adjustment holes; and the knee brace further comprises a first upper pin and a second upper pin, wherein the first upper pin joins the upper cuff to the first upper support arm through one of the one or more adjustment holes, and the second upper pin joins the upper cuff to the first upper support arm through one of the one or more adjustment holes.

8. The knee brace of claim 5, wherein the energy storage member is an o-ring.

9. The knee brace of claim 5, wherein the energy storage member is an elastic band and an energy storage member groove, the energy storage member groove adapted to maintain elastic band tension regardless of flexion angle, where flexion angle is the angle created across the first hinge when the knee brace is bent.

10. The knee brace of claim 5, further comprising a second energy storage member, the second energy storage member attached to only the second upper support arm and the second lower support arm, the energy storage member encouraging the second upper support arm and the second lower support arm into a parallel arrangement.

11. The knee brace of claim 10, wherein the first energy storage member includes a first elastic band positioned within a first groove associated with the first hinge, and the second energy storage member includes a second elastic band positioned within a second groove associated with the second hinge.

12. A knee brace for the rehabilitation and correction of a patient's gait, the knee brace comprising:
    a first upper support arm;
    a second upper support arm;
    a first lower support arm;
    a second lower support arm;
    a upper cuff, the upper cuff connecting the first upper support arm and the second upper support arm;
    a lower cuff, the lower cuff connecting the first lower support arm and the second lower support arm;
    a first hinge, the first hinge joining the first upper support arm and the first lower support arm;
    a second hinge, the second hinge joining the second upper support arm and the second lower support arm;
    a first energy storage member attached to only the first upper support arm and the first lower support arm, the first energy storage member acting to bring the first upper support arm and first lower support arm into a linear arrangement; and
    a second energy storage member attached to only the second upper support arm and the second lower support arm, the second energy storage member acting to bring the second upper support arm and second lower support arm into a linear arrangement.

* * * * *